United States Patent
Shander et al.

(10) Patent No.: US 6,743,419 B1
(45) Date of Patent: *Jun. 1, 2004

(54) METHOD OF REDUCING HAIR GROWTH EMPLOYING SULFHYDRYL ACTIVE COMPOUNDS

(75) Inventors: Douglas Shander, Gaithersburg, MD (US); Gurpreet S. Ahluwalia, Gaithersburg, MD (US); Diana Marks-Del Grosso, Kenington, MD (US)

(73) Assignee: The Gillette Company, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/869,381

(22) Filed: Jun. 5, 1997

Related U.S. Application Data

(63) Continuation of application No. 08/414,992, filed on Mar. 30, 1995, now abandoned, which is a continuation of application No. 07/995,037, filed on Dec. 22, 1992, now Pat. No. 5,411,991.

(51) Int. Cl.⁷ .................... A61K 7/06; A61K 31/225; A61K 31/195; A61K 31/00

(52) U.S. Cl. .................... 424/70.1; 514/562; 514/665; 514/713; 514/547; 514/574; 514/578; 514/711

(58) Field of Search .................... 424/70.1; 514/562, 514/665, 713, 547, 574, 578, 711

(56) References Cited

U.S. PATENT DOCUMENTS

| | | |
|---|---|---|
| 3,426,137 A | 2/1969 | Philpitt et al. |
| 4,039,669 A | 8/1977 | Beyler et al. |
| 4,098,802 A | 7/1978 | van der Vies |
| 4,139,638 A | 2/1979 | Neri et al. |
| 4,161,540 A | 7/1979 | Neri et al. |
| 4,191,775 A | 3/1980 | Glen |
| 4,207,315 A | 6/1980 | Voorhees et al. |
| 4,228,163 A | 10/1980 | Bliss |
| 4,269,831 A | 5/1981 | Ferrari et al. |
| 4,272,508 A | 6/1981 | Tamm |
| 4,310,523 A | 1/1982 | Neumann |
| 4,344,941 A | 8/1982 | Wiechert et al. |
| 4,367,227 A | 1/1983 | Bingham |
| 4,370,315 A | 1/1983 | Greff et al. |
| 4,439,432 A | 3/1984 | Peat |
| 4,456,586 A | 6/1984 | Van der berghe et al. |
| 4,457,925 A | 7/1984 | Bittler et al. |
| 4,463,016 A | 7/1984 | Burgess |
| 4,525,344 A | 6/1985 | Tutsky .................. 424/73 |
| 4,676,978 A * | 6/1987 | Cseh .................... 424/70 |
| 4,684,635 A | 8/1987 | Orenstresch et al. |
| 4,720,489 A | 1/1988 | Shander |
| 4,775,530 A | 10/1988 | Perricone |
| 4,885,289 A | 12/1989 | Breuer et al. |
| 4,912,120 A | 3/1990 | Castelhano et al. |
| 4,929,630 A | 5/1990 | Castelhano et al. |
| 4,935,231 A * | 6/1990 | Pigiet .................... 424/71 |
| 4,944,939 A | 7/1990 | Moore |
| 5,095,007 A | 3/1992 | Ahluwalia |
| 5,096,911 A | 3/1992 | Ahluwalia et al. |
| 5,143,925 A | 9/1992 | Shander et al. |
| 5,362,748 A | 11/1994 | Schwen et al. |

FOREIGN PATENT DOCUMENTS

| | | |
|---|---|---|
| DE | 28 40 144 | 3/1980 |
| GB | 1458349 | 12/1976 |
| JP | 53-127432 | 2/1978 |
| JP | 58-57308 | 4/1983 |
| JP | 61-210021 | 9/1986 |
| JP | 61-289016 | 12/1986 |
| JP | 63-243017 | 10/1988 |
| WO | 9110421 * | 7/1991 |

OTHER PUBLICATIONS

Plewing, The Journal of Investigative Dermatology, 62:308–315 (1974).*
Chemical Abstracts 111: 120611g, 1989.*
Chemical Abstracts 118(14): 131764e, 1992.*
Gahl et al., Biochem. J., 228:545–550 (1985).
Theone et al., Brief Clin. and Lab. Observations, 96:1043–44 (1980).
Theone et al., J. Clin. Invest., 58:180 (1976).
Maiorino et al., The J. of Pharmacology and Experimental Therapeutics, 259:808 (1991).
Walshe, Clinical Studies, pp. 487–495 (Oct. 1956).
Levine, Nature, 187:940 (1960).
Schneider, NE J. Med., 313:1473 (1985).
Porter et al., Adv. Enz. Res., 27:57–59 (1988).
Pegg, Cancer Res., 48:759–74 (1988).
Luk et al., Am. J. Physiol., 254:G194–G200 (1988).
Althonen–Hongisto et al., Biochem. Biphys. Res. Comm., 144:132–137 (1987).
Casero et al., Cancer Res., 47:3964–67 (1987).
Henry et al., Br. J. Derm., 105:33–34 Supplement 20 (1981).
Luk et al., Cancer Res., 42:3070–3073 (1982).
Rupniak et al., Eur. J. Cancer Clin. Oncol., 18:1353–9 (1982).
Peterson et al., Biochem. Biophys. Acta., 657:268–276 (1981).
Kanerva et al., Arch. Toxicol. Suppl (9):455–59 (1986).
Kousa et al., Acta Dermatovener, 62:221–224 (1982).
McCullough et al., J. Invest. Dermatol., 85:518–521 (1985).
McCullough et al., J. Invest. Dermatol., 81:388–392 (1983).
Splinter et al., Eur. J. Cancer Clin. Oncol., 22:61–67 (1986).
Ebling, J. of Investigative Dermatology, 67:98–106 (1976).
Cardo et al., Hair Research 244–250 (1981).
Lucky, Arch Dermatol., 121:55–56 (1985).
Lucky et al., J. Investig. Dermatology, 86:83–86 (1986).

(List continued on next page.)

*Primary Examiner*—Shengjun Wang
(74) *Attorney, Agent, or Firm*—Fish & Richardson P.C.

(57) ABSTRACT

A method of reducing the rate of mammalian hair growth includes topically applying a composition containing a sulfhydryl reactive compound to the skin.

24 Claims, No Drawings

OTHER PUBLICATIONS

Goldberg, "A Method for the Colorimetric Determination of Gamma–Glutamyl Transpeptidase in Human Serum; Enzymatic Activity in Health and Disease", 44:2:127 (1963).
Minato, Arch. of Biochemistry and Biophysics, 192:235–240 (1979).
Gardell et al., Febs Letts, 122:2:171–174 (1980).
Reed et al., Biochemistry and Biophysical Research Communications, 94:4:1273–1277 (1980).
Kim et al., J. of Dermatology 6:39–45 (1979).
Kaszynski, Brit. J. Dermatology, 109:565–569 (1983).
Richards et al., Cancer Research, 42:4143–4151 (1982).
Chase et al., Physiological Zoology, 24:1–8 (1951).
De Young et al., Cancer Research, 38:3697–3701 (1978).
Kinoshita et al., Bull. Chem. Soc. Jpn., 54:2219–2220 (1981).
Chem. Abst., 95–143848, p. 20 (1981).
Gale et al., Biochem. Pharmacology 17:2495–2498 (1968).
Jayaram et al., Biochem. Pharacol. 24:1787–1792 (1975).
Cooney et al., Int. J. Biochem., 11:519–539 (1980).
Van Scott et al., The Journal of Investigative Dermatology, vol. 27 Pages 405–428 (1956).
Rieger, Cosmetics and Toiletries, 101:63–66 (1986).
Downing et al., J. Am. Acad. Dermatol., 14:2:221–222 (1986).
De Young, The Journal of Investigative Dermatology, 82:3:275–279 (1984).
Marsden et al., Pharacology of the Skin II, Chapter 35, pp473–481, 1980.
Mills et al., Cosmetics and Toiletries, vol. 104 (1989).
Pegg et al., The American Physiological Society, pp C212–C221 (1982).
Tyms, The Physiology of Polyamines, vol. II, Chapter I, pp 4–33 (1989).
Spencer, Cosmetics & Toiletries, 100:47–49 (1985).
Dunn, AFP, 39:3:169–174 (1988).
Kligman et al., Arch. Dermatol., 107:551–552 (1973).
Brown, Cutis, 32:373–375 (1983).
Splinter et al., Eur. J. Cancer and Clin. Oncol., 22:61–67 (1986).
Matthews et al., NPhA Journal, pp. 6–12 (Jan. 1982).
Ogawa et al., Curr. Prob. Dermatol., 11:159–170 (1983).
Martinent et al., J. Biol. Chem. 263:4236–4241 (1988).
Folk et al., Adv. Enzymol., 38:109–191 (1973).
Chung et al., Proc. Natl. Acad. Sci. U.S.A., 69:303–307 (1972).
Harding et al., Biochemistry, 11:2858–2863 (1972).
Harding et al., Biochemistry, 10:624–630 (1971).
Goldsmith, Hair Research, pp. 29–35 (1981).
Hattori et al., J. of Dermatology, 10:45–54 (1983).
Killackey et al., Molecular Pharmacology, 35:701–706 (1989).
Scott et al., Transactions, 15:1167–1168 (1987).
Straile, Biology of the Skin and Hair Growth, pp. 35–57 (1965).
Heby, The Physiology of Polyamines, 1:5:83–94 (1988).
Ogawa et al., J. Invest. Dermatol., 68:32–35 (1977).
Chem. Abstracts, vol. 100 (1984) 172302z Ogawa et al.
Burdick et al., Br. J. Derm. (1970) 82, Supplement 6.
Simpson et al., "Bristish Journal of Dermatology", 100:687–692 (1979).
Girard et al., Arch. Dermatol. Res. 269–281–290 (1980).
Goos et al., Arch. Dermatol. Res. (1982) 273:333–341.

* cited by examiner

METHOD OF REDUCING HAIR GROWTH EMPLOYING SULFHYDRYL ACTIVE COMPOUNDS

This is a continuation of application Ser. No. 08/414,992, filed Mar. 30, 1995, now abandoned, which is a continuation of U.S. Ser. No. 07/995,037, filed Dec. 22, 1992, now U.S. Pat. No. 5,411,991.

The invention relates to reducing hair growth in mammals.

Hair proteins include a fairly large quantity of the amino acid cysteine, which includes a thiol (—SH) group. It is the formation of disulfide bonds between cysteine residues in the hair proteins, to form cystine, that give hair its strength and character.

It is known in the art to use depilatory compositions to remove hair from, e.g., legs. Such compositions, when applied to the skin, digest the hair, in part, by breaking down the disulfide bonds in the hair. Such compositions typically include a chemical agent like calcium thioglycolate that aids the digestion process.

We have discovered that the rate of mammalian (including human) hair growth can be reduced by applying a non-depilatory composition including sulfhydryl active compounds to the skin. Sulfhydryl active compounds, as used herein, are compounds that include a free —SH group, thiols without a free —SH group, and thiols or disulfides that can be converted to a moleculer with a free —SH group in cells. Non-depilatory, as used herein, is a composition which after a single topical application does not result in hair removal and/or degradation.

Without being bound to any theory, it is believed that sulfhydryl active compounds reduce hair growth at least in part by one or more of the following mechanisms. During hair growth, cysteine is incorporated into protein chains. The —SH groups of cysteine residues in the protein chains form disulfide bonds (and cystine), binding the protein chains together as part of the normal hair growth. Sulfhydryl active compounds, applied topically, penetrate the hair follicle and interfere with hair growth by (1) reacting with free cysteine to form a mixed cysteine-sulfhydryl active compound disulfide bond, resulting in there being less cysteine available for incorporation into disulfide bonds present in hair proteins; (2) reducing the disulfide bond in cystine in the hair proteins, at the same time forming a mixed cysteine-sulfhydryl active compound disulfide bond; and (3) reducing the disulfide bond in cystine, without concomitant formation of the mixed disulfide bond.

Preferred sulfhydryl active compounds with a free —SH group include thiosalicylic acid, D-cysteine, 2-mercaptoethylamine (cysteamine), captopril, N-acetyl-L-cysteine, cysteinylglycine, 2,3-dimercapto-1-propanesulfonic acid, meso-2,3-dimercaptosuccinic acid, dimethylcysteamine, diethyldithiocarbamic acid, D-penicillamine, L-cysteine methyl ester, and L-cysteine ethyl ester.

Preferred sulfhydryl active compounds without a free —SH group include 3,3'-thiodipropionic acid, isethionic acid, 3-carboxypropyl disulfide, 3,3'-thiodipropionic acid dilauryl ester, sulfasalazine, 3-(methythio)-propylamine, 5'-deoxy-5'-methylthioadenosine, allyl sulfide, DL-α-lipoic acid (reduced form), and DL-methionine-S-methyl-sulfonium chloride.

Preferred sulfhydryl active compounds that are converted to free thiols in cells include phosphocysteamine, which is dephosphorylated to cysteamine in cells; penicillamine disulfide, which is reduced to free penicillamine in cells; and S-2-aminoethyl-L-cysteine, which is hydrolyzed to cysteamine and serine (inactive) in cells.

The sulfhydryl active compounds should not be of too high a molecular weight (greater than about 1000 daltons), or contain highly charged phosphate groups, or compounds that may not adequately penetrate the skin.

The composition contains, in addition to the sulfhydryl active compound, a non-toxic dermatologically acceptable vehicle or carrier which is adapted to be spread on the skin. The concentration of the compound may be varied over a wide range up to a saturated solution, preferably from 1% to 20% by weight. The reduction of hair growth increases as the amount of sulfhydryl active compound applied increases per unit area of skin; the maximum amount that can be effectively applied is limited primarily only by the rate at which the compound penetrates the skin. Generally, the effective amounts range from 100 to 2000. micrograms or more per square centimeter of skin.

The following specific examples in Table 1 are intended to illustrate more clearly the nature of the present invention without acting as a limitation upon its scope. The inhibition in hair growth provided by the sulfhydryl active compounds was determined by following the general procedures described in Shander et al., U.S. Pat. No. 5,132,293, Ahluwalia, U.S. Pat. No. 5,095,007 and Ahluwalia et al., U.S. Pat. No. 5,096,911, both of which are hereby incorporated by reference herein.

TABLE 1

Inhibition of Hair Growth by Sulfhydryl Reactive Compounds

|  |  |  | Hair Mass | | |
| --- | --- | --- | --- | --- | --- |
| Compound | Dose | Vehicle | Treated (mg) | Untreated (mg) | Percent Reduction |
| Thiosalicylic acid | 20% | B | 0.18 ± 0.04 | 1.64 ± 0.04 | 89 ± 2% |
| 2-Mercaptoethylamine (Cysteamine) | 20% | A | 0.30 ± 0.09 | 1.89 ± 0.34 | 86 ± 3% |
| L-Cysteine methyl ester | 20% | A | 0.28 ± 0.07 | 1.91 ± 0.30 | 86 ± 3% |
| L-Cysteine ethyl ester | 20% | A | 0.49 ± 0.08 | 2.73 ± 0.15 | 82 ± 3% |
| N-Acetyl-L-Cysteine | 15% | A | 0.39 ± 0.07 | 2.13 ± 0.31 | 80 ± 4% |
| 2,3,-Dimercapto-1-propanesulfonic acid | 20% | A | 0.64 ± 0.08 | 3.08 ± 0.27 | 79 ± 3% |
| Dimethylaminoethanethiol | 20% | A | 0.34 ± 0.05 | 1.77 ± 0.19 | 78 ± 6% |
| Phosphocysteamine | 25% | E | 0.50 ± 0.10 | 1.94 ± 0.17 | 74 ± 4% |
| 3-Carboxypropyl disulfide | 15% | A | 0.70 ± 0.14 | 2.63 ± 0.26 | 74 ± 4% |
| 3,3'-Thiodipropionic acid | 20% | A | 0.76 ± 0.12 | 2.80 ± 0.25 | 73 ± 4% |
| Diethyldithiocarbamic acid | 15% | A | 0.65 ± 0.09 | 2.28 ± 0.25 | 68 ± 7% |
| D-Penicillamine | 15% | A | 0.57 ± 0.07 | 1.87 ± 0.3 | 65 ± 5% |

TABLE 1-continued

Inhibition of Hair Growth by Sulfhydryl Reactive Compounds

| | | | Hair Mass | | |
|---|---|---|---|---|---|
| Compound | Dose | Vehicle | Treated (mg) | Untreated (mg) | Percent Reduction |
| Sulfasalazine | 20% | C | 0.88 ± 0.14 | 2.32 ± 0.21 | 61 ± 6% |
| D-Cysteine | 10% | A | 1.20 ± 0.17 | 2.92 ± 0.24 | 60 ± 3% |
| 5'-Deoxy-5'-methylthioadenosine | 10% | A | 1.25 ± 0.17 | 2.97 ± 0.27 | 57 ± 6% |
| Captopril | 10% | A | 1.49 ± 0.20 | 3.50 ± 0.15 | 57 ± 5% |
| DL-α-Lipoic acid (reduced form) | 15% | A | 0.74 ± 0.09 | 1.73 ± 0.19 | 56 ± 6% |
| Cystenyl-glycine | 15% | A | 0.93 ± 0.18 | 2.26 ± 0.26 | 55 ± 8% |
| D-Penicillamine disulfide | 15% | A | 1.09 ± 0.23 | 2.36 ± 0.30 | 55 ± 4% |
| Isethionic acid | 15% | A | 1.45 ± 0.22 | 3.03 ± 0.31 | 50 ± 7% |
| meso-2,3,-Dimercaptosuccinic acid | 20% | C | 1.08 ± 0.16 | 2.23 ± 0.28 | 50 ± 5% |
| 3,3'-Thiodipropionic acid dilauryl ester | 20% | D | 1.07 ± 0.10 | 2.15 ± 0.08 | 50 ± 4% |
| S-2-Aminoethyl-L-cysteine | 20% | A | 0.99 ± 0.20 | 2.15 ± 0.35 | 50 ± 11% |
| 3,3'-Thiodipropionic acid dilauryl ester | 5% | D | 1.70 ± 0.21 | 2.39 ± 0.16 | 30 ± 7% |
| 3-(Methylthio)-propylamine | 2% | A | 0.97 ± 0.13 | 1.27 ± 0.10 | 22 ± 13% |
| Allyl sulfide | 20% | B | 1.74 ± 0.16 | 2.22 ± 0.22 | 17 ± 10% |
| DL-∞-Lipoic acid (reduced form) | 5% | B | 2.67 ± 0.26 | 3.22 ± 0.32 | 16 ± 5% |

Vehicles

Vehicle A: 68% distilled $H_2O$, 16% ethanol (100 proof), 5% propylene glycol, 5% dipropylene glycol, 4% benzyl alcohol, 2% propylene carbonate Vehicle B: 80% ethanol (190 proof), 17.5% distilled $H_2O$, 2% propylene glycol dipelargonate (Emerest 2388), 0.5% propylene glycol Vehicle C: Moisturizing lotion containing common cosmetic ingredients which include emulsifiers, detergents, and preservatives Vehicle D: 75% acetone, 20% propylene carbonate, 5% benzyl alcohol Vehicle E: 86% distilled $H_2O$, 4% propylene glycol, 4% dipropylene glycol, 4% propylene carbonate, 2% ethanol The following biochemical properties of some of the sulfhydryl reactive compounds were tested: (1) the percent reduction in hair shaft cysteine caused by the compounds; (2) the ability of the compounds to form a cysteine-mixed disulfide in vitro; (3) the ability of the compound to form a cysteine-mixed disulfide in hair shafts; and (4) the ability of the compounds to reduce cystine.

The percent reduction in hair shaft cysteine caused by the sulfhydryl reactive compounds was measured according to the following procedure. Amino acid analysis of hamster flank organ hairs was carried out using a commercially available amino acid analysis system (Pico-Tag system, available from Waters Associates, Inc., Milford, Mass.). The hairs were thoroughly washed, then hydrolyzed by HCL vapors at 115° C. overnight. The hydrolyzed hairs (now free amino acids) were derivatized with phenylisothiocyanate to yield the phenylthiohydantion derivatives of the respective amino acids, which were then separated by C-18 reverse phase chromatography (HPLC), and quantitated by an in-line UV spectrophotometer. It is believed that the reduction of cysteine levels in hair shafts caused by some of the sulfhydryl active compounds is at least in part responsible for the reduction in hair growth caused by these compounds.

The ability of the sulfhydryl reactive compounds to form cysteine-mixed disulfides in hair shafts was determined according to the following procedure. Groups of eight (8) Golden Syrian hamsters were treated topically with a sulfhydryl active compound on one flank organ (treated site) and the carrier vehicle without the sulfhydryl active compound on the other flank organ (control site). The carrier vehicles were the same as for the results achieved in Table 1. Following thirteen (13) treatments (Mon–Fri, over 18 days), hair shafts from the treated flank organs were harvested and analyzed for the presence of cysteine-mixed disulphides. It is believed that the ability of some of the sulfhydryl reactive compounds to form the cysteine-mixed disulfides in the hair shaft is at least in part responsible for the reduction in hair growth caused by these compounds, as the hair shaft proteins fail to undergo final post-translational maturation (disulfide formation).

The ability of the sulfhydryl reactive compounds to form cysteine-mixed disulfides in vitro was determined by incubating the sulfhydryl reactive compounds in test tubes, with either cystine or cysteine, under physiological conditions (i.e. pH 7.4 and at a temperature of 37° C.). The reaction of these compounds with cysteine or cystine was evaluated by HPLC analysis. It is believed that the ability of a sulfhydryl reactive compound to form a cysteine-mixed disulfide in vitro provides an indication that the compound is capable of forming cysteine-mixed disulfides with free cysteine present in hair follicle bulbs prior to cysteine incorporation into protein of the hair shaft when applied topically to the skin.

The ability of sulfhydryl reactive compounds to reduce cystine was determined by incubating the respective sulfhydryl compound with cystine at physiological conditions of temperature and pH (37 C, pH 7.4). Following the incubation, the samples were derivatized and analyzed on HPLC as given above. For cysteamine, phosphocysteamine and dimethylcysteamine the samples were analyzed without derivatization, using an electrochemical detector instead of the UV detector used in amino acid analysis. The determination of cystine reduction by the compounds was based on generation of cysteine (free thiol) in the incubation mixture. It is believed that reducing the disulfide bond in cystine in hair proteins results in reduced hair growth.

The results of the testing of these properties are recorded in Table 2.

TABLE 2

Biochemical Properties of Select Sulfhydryl Reactive Agents

| Sulfhydryl reactive agent | Percent reduction in hair shaft cysteine | Formation of Cysteine mixed disulfide in-vitro | Formation of Cysteine mixed disulfide in hair shaft | Reduction of Cystine |
|---|---|---|---|---|
| D-Penicillamine | 50% | YES | YES | ND* |
| Cysteamine | 50% | YES | YES | YES |
| Dimethyl cysteamine | 28% | YES | YES | YES |
| Phospho cysteamine | 24% | YES* | YES* | ND* |
| Dimercaptopropanesulfonic acid | 40% | YES | NO | YES |
| Meso-dimercaptosuccinic acid | 22% | NO | ND* | YES |
| Captopril | 26% | YES | ND* | YES |
| 5'-Deoxy methylthioadenosine | 11% | NO | ND* | NO |
| Diethyl dithiocarbamicacid | 18% | NO | ND* | NO |
| Thiosalicylic acid | 14% | NO | ND* | NO |
| Sulfasalazine | (−2%) | NO | ND* | NO |
| Cystienyl-glycine | ND* | ND* | ND* | YES |
| ∝-Lipoic acid | ND* | NO | ND* | NO |

ND*: Not Determined

Other embodiments are within the claims.

What is claimed is:

1. A process of reducing the rate of mammalian hair growth, comprising
   selecting an area of skin from which a reduced rate of hair growth is desired; and
   applying to said area of mammalian skin a non-depilatory composition including a hair growth reducing effective amount of a sulfhydryl active compound selected from the group consisting of 2,3-dimercapto-1-propanesulfonic acid, 3,3'-thiodipropionic acid, isethionic acid, 3-(methylthio)-propylamine, 3,3'-thiodipropionic acid dilauryl ester, allyl sulfide, DL-methionine-S-methyl-sulfonium chloride, penicillamine disulfide, and S-2-aminoethyl-L-cysteine.

2. The process of claim 1 wherein after application said compound penetrates into the hair follicles in said skin and reacts with free cysteine in said hair follicle cells to form cysteine-mixed disulfides.

3. The process of claim 1 wherein said sulfhydryl active compound after application penetrates into the preketanized hair shafts in said skin and reduce the disulfide bond in cystine in hair proteins.

4. The process of claim 3 wherein said sulfhydryl active compound also forms a mixed disulfide bond with one of the cysteine moieties in hair shaft proteins.

5. The process of claim 1 wherein said sulfhydryl active compound is applied to the face.

6. The process of claim 1 wherein said sulfhydryl active compound has a free —SH group.

7. The process of claim 1 wherein said sulfhydryl active compound is a thiol without a free —SH group.

8. The process of claim 1 wherein said sulfhydryl active compound is a thiol or disulfide that can be converted to a molecule with a free —SH group in cells.

9. The process of claim 1, wherein said sulfhydryl active compound is 2,3-dimercapto-1-propanesulfonic acid.

10. The process of claim 1, wherein said sulfhydryl active compound is 3,3'-thiodipropionic acid.

11. The process of claim 1, wherein said sulfhydryl active compound is isethionic acid.

12. The process of claim 1, wherein said sulfhydryl active compound is 3-(methylthio)-propylamine.

13. The process of claim 1, wherein said sulfhydryl active compound is 3,3'-thiodipropionic acid dilauryl ester.

14. The process of claim 1, wherein said sulfhydryl active compound is allyl sulfide.

15. The process of claim 1, wherein said sulfhydryl active compound is DL-methionine-S-methyl-sulfonium chloride.

16. The process of claim 1, wherein said sulfhydryl active compound is penicillamine disulfide.

17. The process of claim 1, wherein said sulfhydryl active compound is S-2-aminoethyl-L-cysteine.

18. The process of claim 1, wherein said non-depilatory composition further comprises a non-toxic, dermatologically acceptable vehicle.

19. The process of claim 18, wherein said composition comprises between 1% and 20% of said sulfhydryl active compound by weight.

20. The process of claim 1, wherein said hair growth that is reduced is androgen-stimulated hair growth.

21. The process of claim 1 wherein said mammalian skin is human skin and said area of human skin to which said composition is applied is an area of skin comprising beard hair.

22. The process of claim 1, wherein said composition, when tested in the Golden Syrian hamster assay, provides a reduction in hair growth of at least 16%.

23. The process of claim 1, wherein said composition, when tested in the Golden Syrian hamster assay, provides a reduction in hair growth of at least 30%.

24. The process of claim 1, wherein said composition, when tested in the Golden Syrian hamster assay, provides a reduction in hair growth of at least 50%.

* * * * *